US012606782B2

(12) United States Patent
Horcajadas Almansa et al.

(10) Patent No.: US 12,606,782 B2
(45) Date of Patent: Apr. 21, 2026

(54) IN VITRO FERTILIZATION SYSTEM AND COMPONENTS ASSOCIATED THEREWITH

(71) Applicant: Overture Life, Inc., New York, NY (US)

(72) Inventors: Jose Antonio Horcajadas Almansa, Alcobendas (ES); Tamara Martin Villalba, Alcobendas (ES); Santiago Munne, Alcobendas (ES); Hannah Victoria Hare, Melbourn (GB); Edwin James Stone, Melbourn (GB); Michael Ian Walker, Melbourn (GB); Jonathan Patrick Casey, Melbourn (GB); Peter Lee Crossley, Melbourn (GB); Alan James Judd, Melbourn (GB); Gary Keith Jepps, Melbourn (GB)

(73) Assignee: Overture Life, Inc., New York, NY (US)

( * ) Notice: Subject to any disclaimer, the term of this patent is extended or adjusted under 35 U.S.C. 154(b) by 771 days.

(21) Appl. No.: 17/886,969

(22) Filed: Aug. 12, 2022

(65) Prior Publication Data

US 2023/0105188 A1    Apr. 6, 2023

Related U.S. Application Data

(63) Continuation of application No. 16/585,499, filed on Sep. 27, 2019, now abandoned.

(30) Foreign Application Priority Data

Sep. 28, 2018    (GB) ...................................... 1815880

(51) Int. Cl.
| | |
|---|---|
| *C12M 3/00* | (2006.01) |
| *A61B 17/435* | (2006.01) |
| *B01L 3/00* | (2006.01) |

(52) U.S. Cl.
CPC ........... *C12M 21/06* (2013.01); *A61B 17/435* (2013.01); *B01L 3/502707* (2013.01); *B01L 2300/0816* (2013.01)

(58) Field of Classification Search
None
See application file for complete search history.

(56) References Cited

U.S. PATENT DOCUMENTS

| | | |
|---|---|---|
| 6,193,647 B1 | 2/2001 | Beebe et al. |
| 2007/0264705 A1 | 11/2007 | Dodgson |
| 2009/0181411 A1 | 7/2009 | Battrell et al. |

(Continued)

FOREIGN PATENT DOCUMENTS

| | | |
|---|---|---|
| WO | 0188087 A2 | 11/2001 |
| WO | 2006097749 A1 | 9/2006 |

(Continued)

OTHER PUBLICATIONS

International Search Report dated Feb. 4, 2020 for PCT/US2019/053416.

(Continued)

*Primary Examiner* — William H. Beisner

(57) ABSTRACT

Described herein are devices, systems, and methods to aid in the manipulation of cells. The devices, methods, and systems disclosed herein can be applied towards, for example, automation of the in vitro fertilization process.

15 Claims, 11 Drawing Sheets

(56) References Cited

U.S. PATENT DOCUMENTS

| | | |
|---|---|---|
| 2010/0015697 A1 | 1/2010 | Junger et al. |
| 2010/0323439 A1 | 12/2010 | Takayama et al. |
| 2011/0183312 A1 | 7/2011 | Huang |
| 2011/0236970 A1 | 9/2011 | Larsen et al. |
| 2016/0133517 A1 | 5/2016 | Delamarche et al. |
| 2016/0278366 A1 | 9/2016 | Craig |
| 2020/0102528 A1 | 4/2020 | Almansa et al. |
| 2020/0318045 A1 | 10/2020 | Jackson-Holmes et al. |
| 2021/0147773 A1* | 5/2021 | Pensabene ............ C12M 21/06 |

FOREIGN PATENT DOCUMENTS

| | | | |
|---|---|---|---|
| WO | WO-2009118014 A1 * | 10/2009 | ............ C12M 23/12 |
| WO | 2010056755 A3 | 12/2010 | |
| WO | 2013004644 A1 | 1/2013 | |
| WO | 2014106286 A1 | 7/2014 | |
| WO | 2016003278 A1 | 1/2016 | |

OTHER PUBLICATIONS

Smith, et al., Application of microfluidic technologies to human assisted reproduction, 2017, Molecular Human Reproduction, vol. 23 (4), pp. 257-268.
Thapa, et al., Microfluidic technology for in vitro fertilization (IVF), 2019, JMST, pp. 1-12.

* cited by examiner

IN VITRO FERTILIZATION SYSTEM AND COMPONENTS ASSOCIATED THEREWITH

CROSS-REFERENCE

This application is a continuation of U.S. patent application Ser. No. 16/585,499, filed Sep. 27, 2019, which claims the benefit of United Kingdom Patent Application No. 1815880.8, filed Sep. 28, 2018, each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

In vitro fertilization (IVF) can be a manual, labor intensive process that requires the services of a highly trained staff. The need for a highly trained staff limits the availability of IVF, while the manual nature of the process can increase costs and lead to a high frequency of errors. Thus, devices, systems, and methods to automate the IVF process have the potential to increase the availability and success rate of IVF.

SUMMARY

In some embodiments, the disclosure provides a method comprising: (a) depositing a group of cells into a well, the well comprising: (i) an open upper end; (ii) a closed lower end; (iii) a perimeter body connecting the closed lower end and the open upper end; (iv) an inlet, wherein a size of the inlet in a first dimension is larger than a diameter of the group of cells and a size of the inlet in a second dimension is smaller than the diameter of the group of cells; (v) an outlet wherein a size of the outlet in a first dimension is larger than the diameter of the group of cells and a size of the outlet in a second dimension is smaller than the diameter of the group of cells; and (b) performing a liquid exchange, wherein the liquid exchange comprises: (I) flowing a first liquid into the well through the inlet; and (II) flowing a second liquid out of the well through the outlet; wherein performing the liquid exchange promotes embryo development of the group of cells.

In some embodiments, the disclosure provides a method of collecting a conditioned media, the method comprising: (a) generating the conditioned media by culturing a group of cells in a media within a well, the well comprising: (i) an open upper end; (ii) a closed lower end; (iii) a perimeter body connecting the closed lower end and the open upper end; (iv) an outlet, wherein a size of the outlet in a first dimension is larger than a diameter of the group of cells and a size of the outlet in a second dimension is smaller than the diameter of the group of cells; (b) connecting a negative pressure port to a storage pot, wherein the storage pot is covered by an air permeable medium and the storage pot is fluidically connected to the well; (c) drawing gas pressure through the negative pressure port out of the storage pot causing the conditioned media to flow through the outlet into the storage pot such that the storage pot fills with the conditioned media and the conditioned media approaches the air permeable medium; and (d) ceasing to draw the conditioned media into the storage pot when the conditioned media contacts the air permeable medium.

In some embodiments, the disclosure provides a biochip comprising: (a) a first layer comprising a plurality of reservoirs; (b) a second layer comprising: (i) a plurality of channels imprinted in the second layer, wherein the channels are in fluidic communication with the reservoirs; (ii) a plurality of valves configured to control liquid flow within the plurality of channels; and (iii) a well imprinted in the second layer fluidically connected to the plurality of reservoirs by the plurality of channels, wherein the well comprises: (I) an open upper end; (II) a closed lower end; (III) a perimeter body connecting the closed lower end and the open upper end; (IV) an inlet; and (V) an outlet wherein the well contains a group of cells, the size of the inlet in a first dimension is larger than a diameter of the group of cells, the size of the inlet in a second dimension is smaller than the diameter of the group of cells, the size of the outlet in a first dimension is larger than the diameter of the group of cells, and the size of the outlet in a second dimension is smaller than the diameter of the group of cells; and (c) a housing encasing the first layer and the second layer.

In some embodiments, the disclosure provides a biochip, an oil, a cryoprotectant, fertilization medium, an embryo culture medium.

In some embodiments, the disclosure provides a system comprising a biochip and an actuation cradle, wherein the biochip fits into the actuation cradle.

DETAILED DESCRIPTION

Figure 1:
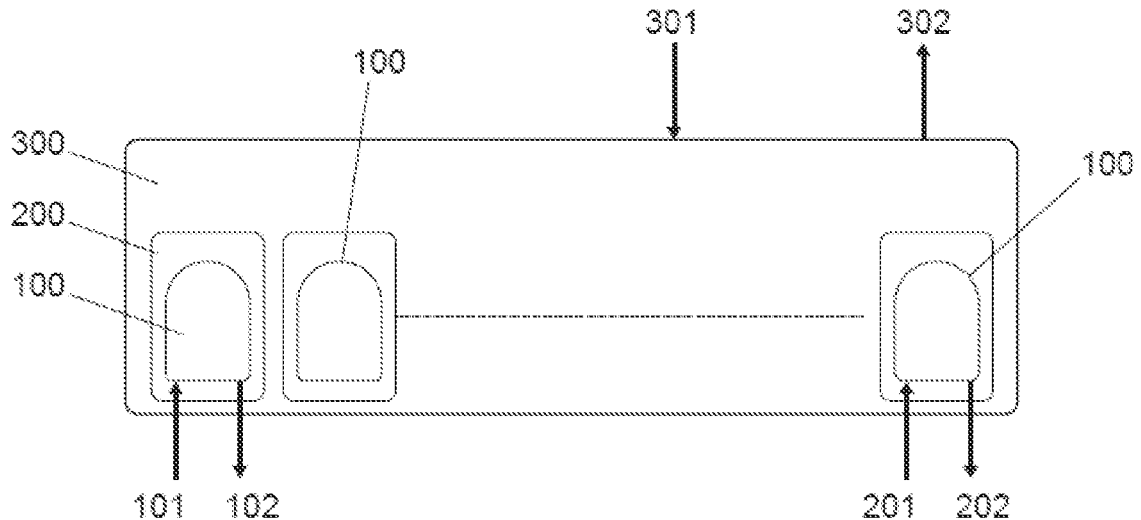
FIG. 1 depicts a diagram showing a system of the disclosure (top view).
Figure 2:
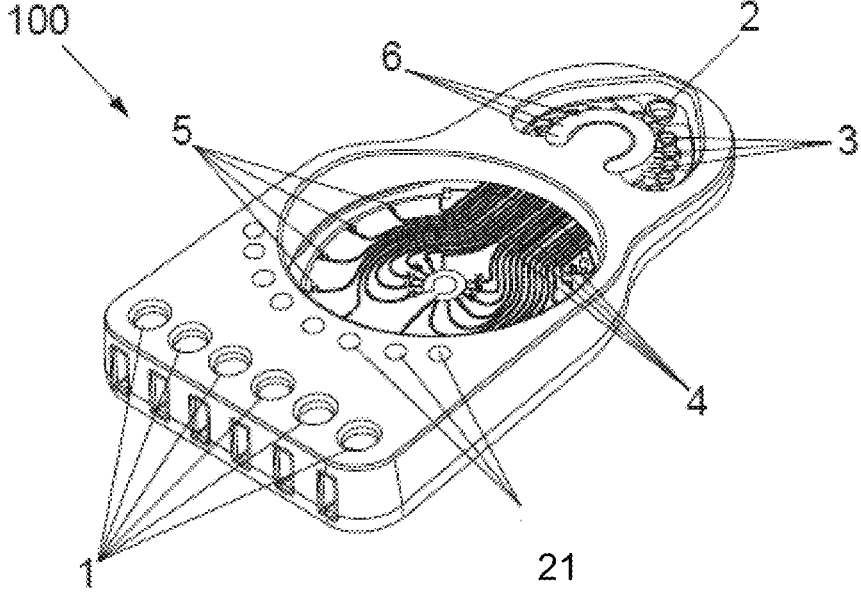
FIG. 2 shows a biochip of the disclosure.
Figure 3:
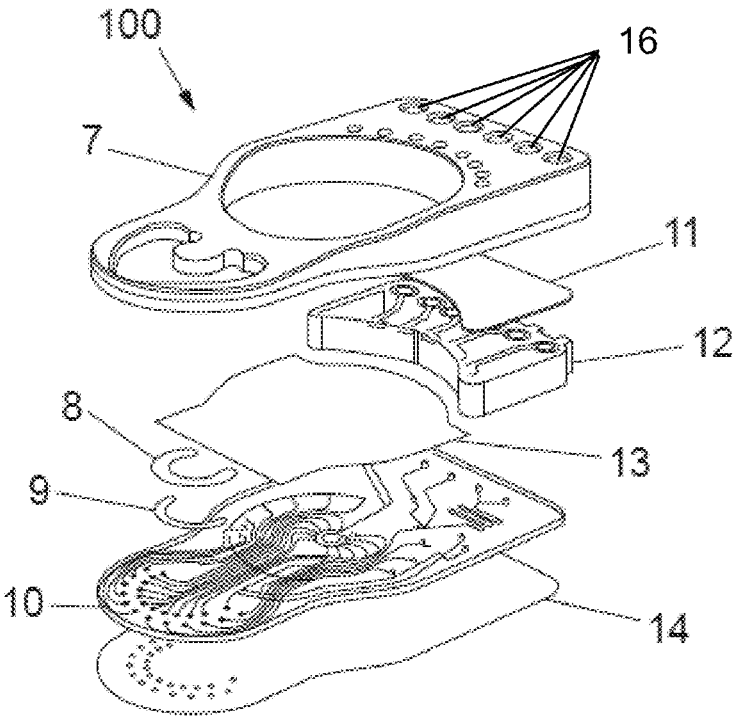
FIG. 3 shows an exploded view of the biochip of FIG. 2.
Figure 4:
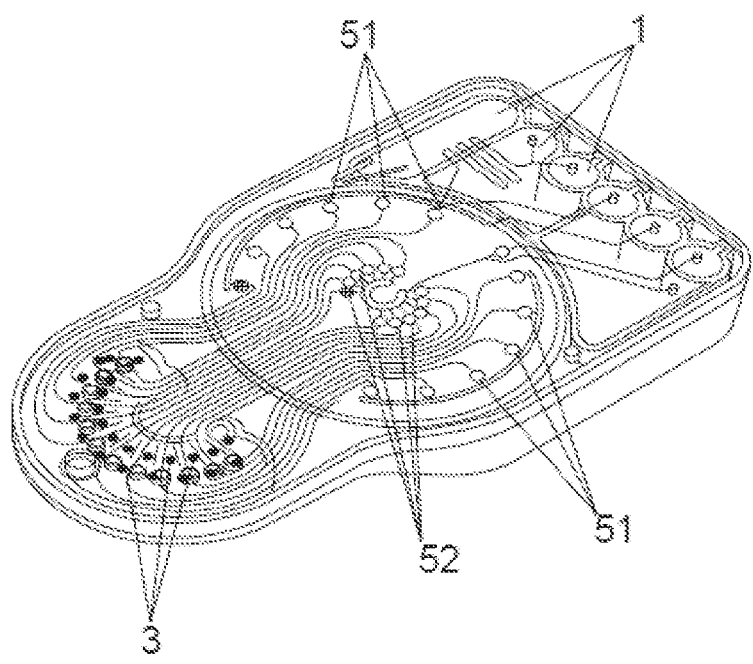
FIG. 4 shows a view from below the biochip of FIG. 2 and FIG. 3.

Described herein are devices, systems, and methods for the manipulating of cells or cell masses. Manipulation of a cell or cell mass can include the fertilization, storage, culture, transfer, or movement of a cell or cell mass. In some embodiments, the cell or cell mass is a one or more reproductive cells such as sperm cells or a group of cells (e.g., embryonic cells). Non-limiting examples of groups of cells that can be manipulated by devices disclosed herein include single cells such as ova and oocytes; and masses of pluralities of cells such as cumulus oocyte complexes, zygotes, embryos, and blastocysts. The manipulation of cells and/or cell masses with a device of the disclosure can aid in the IVF process by, for example, standardizing and/or automating steps of the process.

IVF Process.

IVF involves the fertilization of a female ovum outside of the body. Steps that are frequently performed throughout the IVF process are as follows. Prior to IVF an ovum must be retrieved from a female subject. Non-limiting examples of female subjects include a human, non-human primate, dog, cow, horse, pig, sheep, goat, cat, buffalo, guinea pig, hamster, rabbit, rat, and mouse. Prior to ovum retrieval, a female's ovarian follicles can be stimulated via the administration of one or more hormones or agents including, for example, inhibin, an inhibin and activin mixture, clomiphene citrate, human menopausal gonadotropins such as follicle stimulating hormone (FSH), and a mixture of FSH and luteinizing hormone (LH), and/or human chorionic gonadotropins. Following stimulation, ovarian follicle development can be monitored using ultrasound.

Upon development of ovarian follicles, follicular fluid containing oocytes surrounded by cumulus cells (i.e. the cumulus oocyte complex), can be retrieved. The retrieval of oocytes can occur through various methods including, for example, transvaginal, ultrasound-guided follicular aspiration, perurethral/transvesical ultrasonographic puncture, or through laparoscopic methods. In some embodiments, immature oocytes can be retrieved and allowed to mature in vitro. In some embodiments, oocytes can be developed from ovarian stem cells, mesenchymal stem cells, or ovarian tissue.

Following retrieval, oocytes can be isolated from follicular fluid, washed and placed in a receptacle such as a dish. After about 2 to about 6 hours, eggs are fertilized with sperm via direct injection of sperm into each ovum (intracytoplasmic sperm injection), or by mixing of sperm and oocytes in a dish under conditions that facilitate fertilization. Prior to fertilization, the sperm donor can be analyzed for the number, morphology, and/or motility of sperm. Additionally, sperm will undergo capacitation prior to fertilization. In some instances, capacitation can involve incubation in culture media, washing, migration, density gradients, and filtering of sperm. Capacitation results in the maturation of sperm and can increase the proportion of motile sperm in a sample.

Following insemination, oocytes and sperm are incubated for about 16 hours. Following incubation, the fertilized oocytes (now zygotes), are washed and cultured in vitro in previously prepared cultured dishes to day 3 post fertilization. On day 3 of culture, the embryo culture media is changed and the embryo is cultured to day 5 post fertilization. Embryo culture conditions can include a temperature approximating that found in vivo (37° C.), sub-ambient concentration of oxygen (usually 5%) and elevated concentrations of carbon dioxide (5-6%). In some cases, oil is used to cover embryo cultures to maintain, for example, stable temperature, osmolality, and pH.

Following day 5 post fertilization, embryo biopsy and testing such as preimplantation genetic screening can occur. Embryos can be moved to transfer media, and, in some instances, undergo vitrification. Vitrification can involve moving embryos through increasing concentrations of cryoprotectants, placing embryos on storage devices for cryopreservation, and the storage of embryos in liquid nitrogen.

Following embryo culture (and, in some cases, embryo vitrification/storage), the embryo transfer process can occur. To facilitate embryo transfer, a speculum can be inserted into the vagina of a subject to open the vaginal walls. A catheter is then passed through the cervix and into the uterine cavity. The optimal placement of the catheter within the uterus is 1-2 cm from the uterine fundus, and, in some instances, catheter placement is guided with ultrasound. Following catheter placement, one or more embryos are passed through the catheter and into the uterus where implantation can occur. Implantation of the embryo into the uterine wall results in pregnancy.

At each step of the IVF process, errors can occur that can contribute to an unsuccessful outcome. Steps that involve the physical transfer of an oocyte or embryo or environmental changes of the oocyte or embryo (e.g., media changes and vitrification) can have an increased risk of error. Disclosed herein are devices, systems, and methods that can decrease the risk of error throughout the IVF process. In some embodiments, devices, systems, and methods of the disclosure can facilitate the automation of the preparation of embryo culture dishes, isolation of oocytes from follicular fluid, sperm capacitation, insemination, oocyte and embryo incubation and culture steps, media changes, embryo biopsy and testing, embryo vitrification, and embryo storage. By decreasing the amount of human input needed for the aforementioned steps, the likelihood of errors and variability occurring during the IVF process can be decreased. Further, use of devices, systems, and/or methods disclosed herein can minimize oocyte/embryo disruption, minimize embryo/oocyte environmental changes, minimize physical transfers of embryos/oocytes, allow for the time-lapse monitoring of embryos without disruptions for media exchange, improve reliability of the IVF process, de-skill the IVF process, allow for automated sampling of embryo culture media and non-invasive embryo analysis, improve the selection of potentially viable embryos, and reduce the risk of errors in embryo traceability.

Biochip.

Disclosed herein is a biochip for the manipulation of cells or cell masses including, for example, ova, oocytes, sperm cells, zygotes, embryos, and blastocysts. In some embodiments, the biochip comprises a well, reservoirs, a plurality of channels selectively connectable to the reservoirs and the well, and a plurality of valves arranged to control the connection between the reservoirs and the well. In some embodiments, the well can be used to receive and/or manipulate a cell or cell mass (e.g., an oocyte, zygote, embryo, or blastocyst). In some embodiments, reservoirs can be used to retain fluids used in the processing of a cell or cell mass. In some embodiments, the channels and valves are arranged such that only one reservoir can be connected to the well at any one time. The well, channels, and valves can be arranged such that a plurality of steps within the IVF process can be performed on a cell or cell mass such as an oocyte, zygote, embryo, or blastocyst within the biochip. In some embodiments, a vitrification method can be performed on a cell or cell mass within the biochip.

Channels of a biochip disclosed herein can be, for example, microfluidic channels. Fluid can be driven through channels by, for example, pneumatic, hydraulic, or gravity forces. In some embodiments, the channels of a biochip can be sealed from the top side of a biochip and from the bottom side of a biochip. In some examples, channels are sealed on the top side of the biochip by a first or upper film and are sealed on the lower side of the biochip by a second or lower film. Upper and/or lower films can be made up of various materials. Non-limiting examples of materials that can make up an upper or lower film include polystyrene, cyclic olefin copolymers, thermoplastics, and elastomers.

A biochip of the disclosure can further comprise input ports (also referred to herein as inputs) and/or output ports. Inputs can allow for the entry of, for example, sperm, fertilization media, incubation (embryo culture) media, oocytes, oil, and/or vitrification solution into a biochip. Output ports (also referred to herein as outputs) can allow for the release of, for example, blastocysts, or sample media from a biochip. Once inserted into a biochip through an input, the inputted material can flow through the plurality of channels of the biochip and into wells or reservoirs present within the biochip. In some embodiments, material inserted through an input can be stored in a tray. A tray can comprise one or more reservoirs, each reservoir for the storage of a different inputted material (e.g., sperm, vitrification reagents/cryoprotectants, fertilization media). In some embodiments, a tray can comprise a separate waste reservoir. Reservoirs can be fluidically connected to channels within the biochip to allow for the transfer of materials out of a reservoir to other locations within the biochip. In some embodiments, a reservoir can comprise a structure to prevent overfilling or incorrect filling. In some embodiments, a seal or membrane is located over each reservoir. A seal or membrane can, in some instances, maintain a gas tight seal for maintaining air pressures that allow for the control of fluid movements. In some embodiments, one seal or membrane covers all reservoirs of a biochip. In some embodiments, one seal or membrane covers multiple reservoirs of a biochip. In some embodiments, each reservoir is covered by a different seal or membrane. In some embodiments, the seal or membrane is an elastomer seal or membrane.

In some embodiments, a biochip of the disclosure comprises storage pots (also referred to herein as pots). The viability of an embryo can, in some instances, be predicted through testing of the embryo's culture media. In some embodiments, a biochip of the disclosure is arranged so that a small volume of fluid can be extracted from each well. For example, a storage pot can be connected to a well via a microfluidic channel and a negative pressure applied to the headspace of the pot can pull a fluid sample from the well into the pot. Alternatively, a positive displacement plunger can be used to move a fluid sample from a well to a storage pot. Extracted fluid can be stored in storage pots for later retrieval. For example, the media stored in storage pots can be retrieved after embryo culture, and/or before embryo transfer or vitrification. In some embodiments, an air permeable medium (e.g., filter paper, a hydrophobic filter, or a hydrophobic membrane) is used to cover storage pots and prevent overfilling. In some embodiments, a foil covering covers and/or protects media stored in storage pots. A foil covering can, in some instances, be placed on top of filter paper that is covering storage pots. In some embodiments, a foil can create a seal that allows a negative pressure to build up. In some embodiments, a user can retrieve media stored in a storage pot by breaking the foil.

A biochip of the disclosure can comprise a cover. A cover can, for example, encase one or more other components of a biochip.

Wells.

A well of a biochip of the disclosure can, in some instances, be accessible to a user from the top. For example, a well can be open from the top to allow a user to deposit an oocyte or embryo into the well. In some instances, a removeable cover can be placed on top of the well following deposition of an oocyte. In some instances, wells are transparent. The number of wells in a biochip can vary. For example, a biochip can have 1, 2, 3, 4, 5, 6, 7, 8, 9, 10, 11, 12, 13, 14, 15, 16, 17, 18, 19, 20, 21, 22, 23, 24, 25, or more than 25 wells. In some embodiments, a biochip can have at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 wells. In some embodiments, an oocyte can be fertilized by sperm in a well and the fertilized oocyte matures in the well. Maturation can take place, for example, up until the zygote, embryo, or blastocyst stage. In some embodiments, a zygote, embryo, or blastocyst can be cultured in a well.

In some embodiments, a well of a biochip of the disclosure can comprise one or more inlets and one or more outlets. In some embodiments, the inlets and outlets are sized such that fluid can flow through the inlet or outlet into and out of the well, but an oocyte, embryo, zygote, or blastocyst is unable to flow out of the well. For example, each inlet and outlet of a well can be smaller than an oocyte, embryo, zygote, or blastocyst in one dimension (to trap the cell or cell mass within the well), but larger than the oocyte, embryo, zygote, or blastocyst in another dimension (to prevent blockage by the cell or cell mass and allow fluid flow into and out of the well). In some embodiments, a cell or cell mass remains within the same well of a biochip throughout multiple, or all, steps of the IVF process. In some embodiments, a cell or cell mass is held within a well by suction.

An inlet or an outlet can have, for example, a rectangular or elliptical cross section. Both rectangular and elliptical cross sections can have two dimensions, a length and width or a major axis and minor axis, respectively. In some embodiments, an inlet or outlet of the disclosure has a first dimension with a size of about 120 μm to about 500 μm. In some embodiments, an inlet or outlet of the disclosure has a first dimension with a size of about 120 μm to about 160 μm, about 120 μm to about 180 μm, about 120 μm to about 200 μm, about 120 μm to about 250 μm, about 120 μm to about 300 μm, about 120 μm to about 350 μm, about 120 μm to about 400 μm, about 120 μm to about 450 μm, about 120 μm to about 500 μm, about 160 μm to about 180 μm, about 160 μm to about 200 μm, about 160 μm to about 250 μm, about 160 μm to about 300 μm, about 160 μm to about 350 μm, about 160 μm to about 400 μm, about 160 μm to about 450 μm, about 160 μm to about 500 μm, about 180 μm to about 200 μm, about 180 μm to about 250 μm, about 180 μm to about 300 μm, about 180 μm to about 350 μm, about 180 μm to about 400 μm, about 180 μm to about 450 μm, about 180 μm to about 500 μm, about 200 μm to about 250 μm, about 200 μm to about 300 μm, about 200 μm to about 350 μm, about 200 μm to about 400 μm, about 200 μm to about 450 μm, about 200 μm to about 500 μm, about 250 μm to about 300 μm, about 250 μm to about 350 μm, about 250 μm to about 400 μm, about 250 μm to about 450 μm, about 250 μm to about 500 μm, about 300 μm to about 350 μm, about 300 μm to about 400 μm, about 300 μm to about 450 μm, about 300 μm to about 500 μm, about 350 μm to about 400 μm, about 350 μm to about 450 μm, about 350 μm to about 500 μm, about 400 μm to about 450 μm, about 400 μm to about 500 μm, or about 450 μm to about 500 μm. In some embodiments, an inlet or outlet of the disclosure has a first dimension with a size of about 120 μm, about 160 μm, about 180 μm, about 200 μm, about 250 μm, about 300 μm, about 350 μm, about 400 μm, about 450 μm, or about 500 μm. In some embodiments, an inlet or outlet of the disclosure has a first dimension with a size of at least about 120 μm, at least about 160 μm, at least about 180 μm, at least about 200 μm, at least about 250 μm, at least about 300 μm, at least about 350 μm, at least about 400 μm, or about at least 450 μm. In some embodiments, an inlet or outlet of the disclosure has a first dimension with a size of at most about 160 μm, at most about 180 μm, at most about 200 μm, at most about 250 μm, at most about 300 μm, at most about 350 μm, at most about 400 μm, at most about 450 μm, or at most about 500 μm.

In some embodiments, an inlet or outlet of the disclosure has a second dimension with a size of about 1 μm to about 60 μm. In some embodiments, an inlet or outlet of the disclosure has a second dimension with a size of about 1 μm to about 10 μm, about 1 μm to about 20 μm, about 1 μm to about 30 μm, about 1 μm to about 40 μm, about 1 μm to about 50 μm, about 1 μm to about 60 μm, about 10 μm to about 20 μm, about 10 μm to about 30 μm, about 10 μm to about 40 μm, about 10 μm to about 50 μm, about 10 μm to about 60 μm, about 20 μm to about 30 μm, about 20 μm to about 40 μm, about 20 μm to about 50 μm, about 20 μm to about 60 μm, about 30 μm to about 40 μm, about 30 μm to about 50 μm, about 30 μm to about 60 μm, about 40 μm to about 50 μm, about 40 μm to about 60 μm, or about 50 μm to about 60 μm. In some embodiments, an inlet or outlet of the disclosure has a second dimension with a size of about 1 μm, about 10 μm, about 20 μm, about 30 μm, about 40 μm, about 50 μm, or about 60 μm. In some embodiments, an inlet or outlet of the disclosure has a second dimension with a size of at least about 1 μm, at least about 10 μm, at least about 20 μm, at least about 30 μm, at least about 40 μm, at least or about 50 μm. In some embodiments, an inlet or outlet of the disclosure has a second dimension with a size of at most about 10 μm, at most about 20 μm, at most about 30 μm, at most about 40 μm, at most about 50 μm, or at most about 60 μm.

Figure 8:
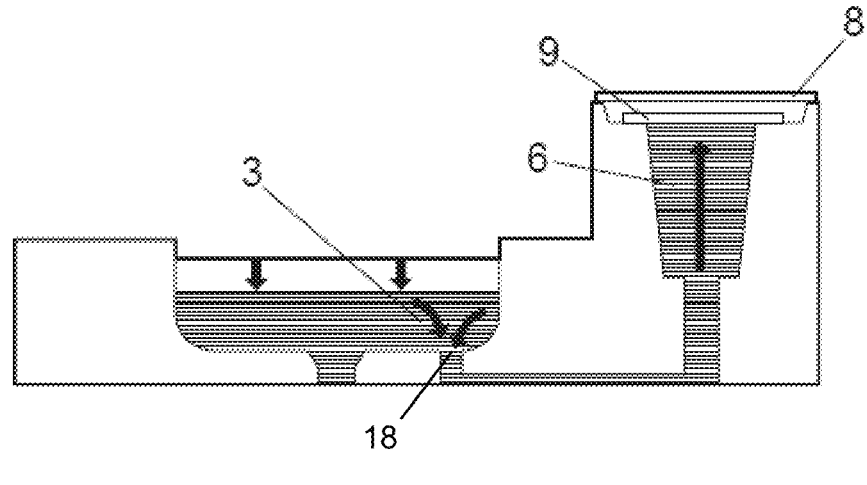
FIG. 8 shows a cross sectional view of a sampling system.

In some embodiments, a well of the disclosure can comprise a suction port. A suction port (18) as shown in FIG. 8 can, in some instances, be used to hold a cell or cell mass at a single location within a well. For example, a negative pressure applied to a suction port can cause an oocyte, embryo, or blastocyst to remain pressed against the suction port.

Channels.

A biochip disclosed herein can comprise a plurality of channels. Channels can be selectively connectable to different components of a biochip such as, for example, reservoirs, wells, storage pots, input ports, and output ports. Channels of a biochip disclosed herein can be the same or different sizes. In some embodiments, a channel of the disclosure has a diameter of about 1 μm to about 10,000 μm. In some embodiments, a channel of the disclosure has a diameter of about 1 μm to about 5 μm, about 1 μm to about 10 μm, about 1 μm to about 50 μm, about 1 μm to about 100 μm, about 1 μm to about 200 μm, about 1 μm to about 300 μm, about 1 μm to about 500 μm, about 1 μm to about 1,000 μm, about 1 μm to about 2,000 μm, about 1 μm to about 5,000 μm, about 1 μm to about 10,000 μm, about 5 μm to about 10 μm, about 5 μm to about 50 μm, about 5 μm to about 100 μm, about 5 μm to about 200 μm, about 5 μm to about 300 μm, about 5 μm to about 500 μm, about 5 μm to about 1,000 μm, about 5 μm to about 2,000 μm, about 5 μm to about 5,000 μm, about 5 μm to about 10,000 μm, about 10 μm to about 50 μm, about 10 μm to about 100 μm, about 10 μm to about 200 μm, about 10 μm to about 300 μm, about 10 μm to about 500 μm, about 10 μm to about 1,000 μm, about 10 μm to about 2,000 μm, about 10 μm to about 5,000 μm, about 10 μm to about 10,000 μm, about 50 μm to about 100 μm, about 50 μm to about 200 μm, about 50 μm to about 300 μm, about 50 μm to about 500 μm, about 50 μm to about 1,000 μm, about 50 μm to about 2,000 μm, about 50 μm to about 5,000 μm, about 50 μm to about 10,000 μm, about 100 μm to about 200 μm, about 100 μm to about 300 μm, about 100 μm to about 500 μm, about 100 μm to about 1,000 μm, about 100 μm to about 2,000 μm, about 100 μm to about 5,000 μm, about 100 μm to about 10,000 μm, about 200 μm to about 300 μm, about 200 μm to about 500 μm, about 200 μm to about 1,000 μm, about 200 μm to about 2,000 μm, about 200 μm to about 5,000 μm, about 200 μm to about 10,000 μm, about 300 μm to about 500 μm, about 300 μm to about 1,000 μm, about 300 μm to about 2,000 μm, about 300 μm to about 5,000 μm, about 300 μm to about 10,000 μm, about 500 μm to about 1,000 μm, about 500 μm to about 2,000 μm, about 500 μm to about 5,000 μm, about 500 μm to about 10,000 μm, about 1,000 μm to about 2,000 μm, about 1,000 μm to about 5,000 μm, about 1,000 μm to about 10,000 μm, about 2,000 μm to about 5,000 μm, about 2,000 μm to about 10,000 μm, or about 5,000 μm to about 10,000 μm. In some embodiments, a channel of the disclosure has a diameter of about 1 μm, about 5 μm, about 10 μm, about 50 μm, about 100 μm, about 200 μm, about 300 μm, about 500 μm, about 1,000 μm, about 2,000 μm, about 5,000 μm, or about 10,000 μm. In some embodiments, a channel of the disclosure has a diameter of at least about 1 μm, at least about 5 μm, at least about 10 μm, at least about 50 μm, at least about 100 μm, at least about 200 μm, at least about 300 μm, at least about 500 μm, at least about 1,000 μm, at least about 2,000 μm, or at least about 5,000 μm. In some embodiments, a channel of the disclosure has a diameter of at most about 5 μm, at most about 10 μm, at most about 50 μm, at most about 100 μm, at most about 200 μm, at most about 300 μm, at most about 500 μm, at most about 1,000 μm, at most about 2,000 μm, at most about 5,000 μm, or at most about 10,000 μm.

Valves.

Valves of a biochip disclosed herein can control the flow of fluid through a biochip. Valves can be located, for example, within or at the end of channels. A biochip of the disclosure can comprise any combination of types of valves such as, for example rotating valves, shuttle valves, gate valves, and membrane valves. Rotating valves work by rotating a portion of a channel perpendicularly to rest of the channel. Shuttle valves work by displacing a portion of a channel linearly to misalign the portion with the rest of the channel. Gate valves block a channel with a moving pin or gate. When a membrane valve is used a piece of material is deflected or stretched to block a port leading to a channel or to block a channel directly. In some embodiments, valves of a biochip disclosed herein are configured such that only one reservoir is connected to a well at any one time. Valves disclosed herein can be operated by, for example, an actuation electromechanical device hereinto referred to herein as a cradle.

Cradles.

A biochip of the disclosure can be part of a system. A system disclosed herein can, in some instances, comprise an actuation cradle (also referred to herein as a cradle). In some instances, a biochip can be inserted into a cradle. A cradle can interface mechanically and/or pneumatically with a biochip. In some embodiments, a cradle comprises a plurality of actuation pins for engaging with valves of a biochip. The activation pins can be controlled by the cradle to selectively operate the valves to control fluid flow. Activation pins can be controlled by, for example, a microprocessor. Control can be dependent upon instructions set as pre-programmed on the microprocessor or controlled either directly or wirelessly through a remote-control mechanism.

In some embodiments, a cradle operates valves to perform at least one operation associated with IVF.

A cradle disclosed herein can comprise, for example, any combination of valves, pumps, sensors, electronics, and power supplies. In some embodiments a cradle comprises an internal power supply such as a battery. In some instances, the battery is a rechargeable battery. In some instances, a cradle disclosed herein can monitor the battery level of the cradle and power down certain capabilities when the battery is below a critical level. In some embodiments, a cradle is connected to an electrical supply. In some embodiments, a valve of a cradle is an electromechanically operated valve such as a solenoid valve. In some embodiments, a cradle comprises a temperature control unit such as a heater. In some instances, a temperature control unit can hold the temperature of a biochip at 37° C. for 1, 2, 3, 4, 5, 10, 15, 20, 25, 30, 60, 120, 180, 240, 300, or more minutes.

A cradle can comprise one or more pumps, for example 1, 2, 3, 4, 5, 6, 7, 8, 9, 10, 11, 12, 13, 14, 15 or more pumps. Pumps of a cradle can provide positive or negative air or hydraulic pressure. For example, a cradle can pressure the air in reservoirs above media to push media to wells or can apply negative pressure to an air space on top of storage pots or a waste reservoir. Non-limiting examples of pumps include pressure pumps, syringe pumps, membrane pumps, peristaltic pumps, piston pumps, turbine pumps, and capillarity-based passive pumps.

A cradle disclosed herein can comprise sensors. Non-limiting examples of sensors include temperature sensors, pressure sensors, flow sensors, sensors to monitor reservoir, well, and/or storage pot volume, and capacitive sensors.

In some embodiments, a cradle can determine the liquid level in the wells, reservoirs, and/or storage pots of a biochip. For example, a sensor of a cradle can detect the exact level of an oil water interface in a well, or can detect when fluid drops below, or rises above, a critical level. In some instances, sensing can be used to prevent emptying or overfilling of wells, storage pots, and/or reservoirs. In some embodiments, fluid level can be detected with capacitive sensors, which detect a change in capacitance between two electrodes due to a change in the fluid level of a well, storage pot, or reservoir. Capacitive sensors can be implemented as pads on a printed circuit board. Pads can be interdigitated to increase the fringing fields which will sense liquids above them. Detection of liquid level can enable closed loop control of the fluid level in each well, reservoir, or storage pot.

In some embodiments, a cradle can be arranged so that it can identify and/or verify a biochip. In some instances, a cradle disclosed herein can interrogate a biochip to read a unique identifier. For example, a biochip can be encased in a housing with an identifier on the housing that can be recognized by the cradle. Non-limiting examples of identifiers include, for example, a bar code, a quick response (QR) code, a two-dimensional bar code, a radio frequency identification (RFID) tag, machine recognizable text, machine recognizable symbols, and an electronic chip. In some embodiments, a cradle can recognize text or symbols presented on a biochip disclosed herein. Identification of a biochip can ensure, for example, the safety and reliability of the IVF process, that authorized parts are used, that biochips are not reused, and that the correct workflow can be selected for the biochip that is being used with the cradle.

A cradle can comprise components to input and output information. For example, a cradle disclosed herein can receive information such as patient data and process protocols and output information such as data related to the IVF process.

In some instances, a cradle can provide feedback to a user regarding a process (e.g., IVF) taking place in a biochip. Non-limiting examples of ways by which a cradle can provide feedback include light emitting diodes (LEDs) under each well, LEDs under reagent reservoirs, LEDs, on top of the cradle, a display on top of the cradle, a buzzer, a speaker, and a sounder. Cradles disclosed herein can provide feedback regarding, for example, incubation times, liquid levels in reservoirs, liquid levels in wells, liquid levels in storage pots, temperatures, and pressures within a biochip.

Cradles disclosed herein can communicate with other devices. Communication with other devices can occur, for example, with a wireless interface. Communication via a wireless interface allows the cradle to communicate wirelessly with other parts of the system, such as the incubator which may act as an interface to other wireless and network technologies, and such as an automated cryopreservation device. Common devices such as smart phones, tablets and PCs can communicate with the system which would forward them on to the cradle. To ensure robust communications around a lab environment, cradles can form a mesh network. A cradle disclosed herein can communicate wirelessly over protocols supported by common smartphones and tablets e.g. Bluetooth or wireless internet so the cradle can communicate directly with other devices. This communication can be used to record device recordings, for example, temperature. In some examples, a wireless communication can be used to trigger biochip actions from a user interface to start cryo-preparation.

A cradle disclosed herein can ensure traceability by, for example, maintaining a complete record of everything that has happened to it. In some instances, a cradle can maintain a record of temperatures and when it has been removed from the incubator.

In some embodiments, a cradle can have processing capability independent of the rest of a system and can have one or more micro-controllers on board. Independent processing capability can allow a cradle to operate independently or semi-independently of the rest of the system and/or components parts of the system (e.g., an incubator).

Incubators.

A system disclosed herein can comprise an incubator. A biochip and cradle disclosed herein can be constructed so that the biochip and cradle can be placed in an incubator. In some embodiments, an incubator disclosed herein houses several biochip/cradle combinations. An incubator disclosed herein can control and maintain the gas environment in which oocytes and embryos develop. In some instances, an incubator allows for the development of oocytes and embryos to be viewed using microscopy. An incubator disclosed herein can also carry out additional functions. For example, an incubator of the disclosure can take regular images of all oocytes/embryos for time lapse data; maintain a robust record of the patient data, biochip and cradle identifications and acquired images (this could be in the cloud); and allow users to input desired protocols and track embryo progress (this could be integrated or accessed via an external or separable screen).

Downstream Analysis.

A biochip can be structured to be taken to an analysis instrument (e.g., a microscope). Downstream analysis can be of any type, and automated transfer of the sample from a biochip to an analysis instrument can occur.

EXAMPLES

Example 1: IVF System and Use Thereof

An IVF system comprises the following elements as shown in FIG. 1: a biochip (100), a cradle (200), and an incubator (300).

The biochip (100) is a consumable, one per patient (able to process multiple oocytes/embryos) which is cheap to manufacture, and holds media, oocytes, sperm, and/or embryos.

The cradle (200) is re-usable; contains valves, pumps, pressure sensors, temperature sensors, electronics, battery and generally is set up in the system with one required per biochip (100) in use. The cradle (200) controls temperature and fluid flows within the biochip (100) and ensures traceability.

For the incubator (300), there is usually one or more required per lab, and it holds many (typically 6-20) biochips (100) and cradles (200). The incubator (300) provides environmental control (e.g., gas and temperature control). The incubator can contain an optical system for time-lapse imaging of the embryo and can control data storage with the ability to upload data to a remote site. The incubator can also provide a graphical user interphase (GUI) for the user to input desired protocols and to monitor progress of embryos during incubation. The (GUI) can be integrated into the system, or can be external/separable.

The incubator (300) can house up to several cradles (200), each cradle connected to a biochip (100). Each biochip (100) has inputs (media, sperm, oocytes, etc.) and outputs (blastocysts, sample media, etc.). Further, each cradle (200) has inputs (patient data, process protocol, etc.) and outputs (process data, etc.). At the same time, the incubator (300) also has inputs (main power, gases, etc.) and outputs (imaging data, gas control data, temperature control data, etc.).

As shown in FIG. 2, FIG. 3, FIG. 4, and FIG. 5, the biochip (100) comprises:

a chip (10) that contains all the microfluidic channels (4), valves (5), wells (2), (3) and pots (6), a cover (7), that makes the biochip (100) look clean and simple, a lower film (14), that seals the microfluidic channels on the bottom of the chip, an upper film (13), that seals the microfluidic channels on the top of the chip, leaving the wells and pots open through its upper side, a tray (12), containing reservoirs (1) for holding fluids/reagents, such as oil, incubation medium, cryoprotectant solutions (i.e., vitrification solutions), fertilization medium or sperm among others, a seal (11), over the tray, for maintaining air pressures required to control fluid movement, a foil (8), that covers and protects media samples, and a filter paper (9), that prevents media samples from overfilling pots (6)

In the biochip (100) reagent fluids are loaded into reservoirs (1). The loading can either be done by the manufacturer of the biochip (100) or transferred by an embryologist from a standard supply format. In the case of the latter, illuminated prompts and/or color-coding are used to ensure the reagents are transferred into the correct reservoir (100). As mentioned, the reservoirs (1) can contain oil, incubation medium, cryoprotectants (i.e., vitrification solutions) fertilization medium or sperm among others as reagents.

A seal or membrane (11) over each input reservoir maintains a gas tight seal for maintaining air pressures needed to control fluid movements.

Fluid flows through the biochip (10) due to positive and/or negative air pressure in the air cavity within the reagent reservoir (1) above the reagent. An alternative approach is to use displacement-driven flow, for example, by using syringe pumps, piston pumps, piezoelectric diaphragm pumps, peristaltic pumps which may act directly on the fluid channels (4).

There is one functional well (3) per oocyte/embryo for fertilization/culture/cryo-exchange, and optionally at least one extra non-functional well (2), or working well, for temporarily holding oocytes or embryos, making it easier for the user to load the functional wells (3). The number of oocytes/embryos can vary, a balance can be struck between efficient processing of cycles through a clinic and the complexity of the biochip (100).

Figure 6A:
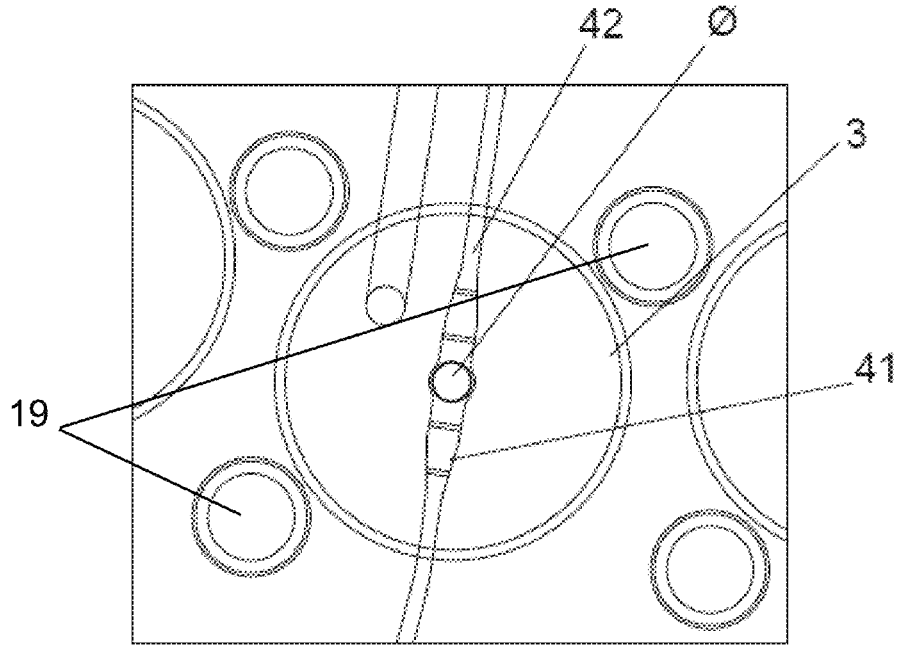
FIG. 6A shows a top view of a functioning well including inlet and outlet channels.
Figure 6B:
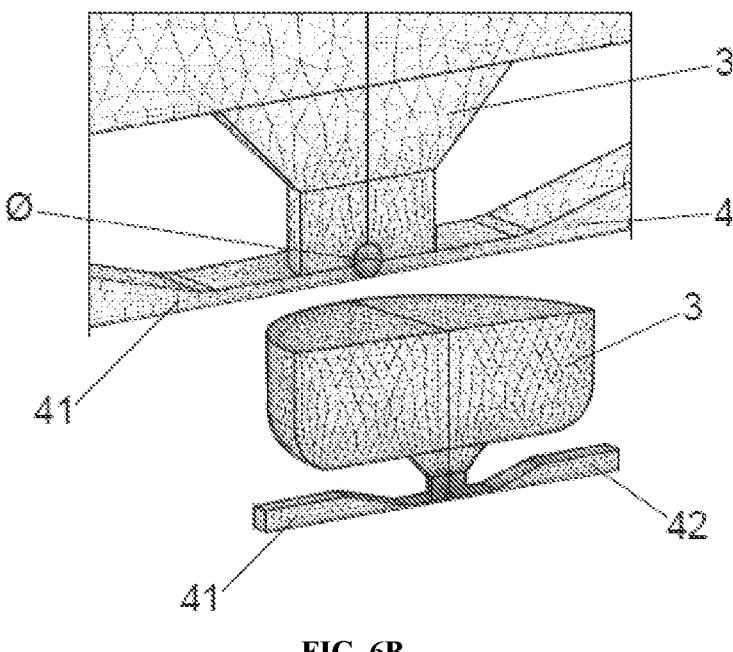
FIG. 6B shows a cross section of a functional well and a detail of the same.

As shown in FIG. 6A and FIG. 6B, each functional well (3) (hereinafter referred to simply as a "well") has both an inlet (41) and an outlet (42) channel. The well (3) is generally open, with manual access from the open top and fluidic access from inlet (41) and outlet channels (42) at the base. Each inlet (41) and outlet (42) channel is smaller than an oocyte in one dimension (to trap the oocyte inside the well [3]) but larger than the oocyte in another dimension (to prevent complete blocking by an oocyte and to allow fluid to flow around the oocyte). Specifically, FIG. 6A shows a top view of one functional well (3) (of approx. 0.5 mm) with an oocyte or embryo (0) inside including inlet (41) and outlet (42) channels. FIG. 6B shows a cross section and a detail of the same, where it can be seen the narrow height of the channels (41), (42) to trap the oocyte/embryo. Similar functionality can be provided in an alternative well system with plural inlet (41) and outlet (42) channels for each well. Another alternative can comprise only one inlet channel (41) and at least two, or more, outlet channels (42).

The channels are rectangular and are 10-60 μm in one dimension, 120-500 μm in the other.

In general, the shape of well (3) fulfills the following functions:

provides easy access for the user to place and retrieve oocytes/embryos;

the oocytes are reliably located in a small enough area to be compatible with an imaging system of manageable performance, cost and complexity (a field of view in the range of 400-1000 μm diameter would be typical);

the oocytes should not be subjected to significant stresses (for example mechanical, thermal or chemical) when fluid exchange occurs; and the oocytes should not move far from their initial position (for example oocytes should not float upwards during fluid exchange and out of the focal place of the optical system). The oocytes may be held by suction, for example during an ICSI process.

The well (3) is open, but a lid is provided to prevent flooding on the biochip (100).

The material of the wells (2, 3) is transparent from both above and below to allow for illumination and oocyte/embryo imaging. Fluid is routed from input reservoirs (1) into and out of any given well (3), and to waste. A series of valves (5) control these fluid flows, driven by positive and/or negative pressure applied to the headspace of the fluid reservoirs (1) (including the waste reservoir).

Example 2: Biochip Functions

A biochip is manufactured with the capability to carry out the following functions:

a. Media equilibration
b. Priming of microfluidic channels
c. Filling wells (3) with media and covering them with oil to control gaseous exchange.
d. Fertilization, which involves one of:
  i. Moving sperm into the well (3),
  ii. Moving sperm near the well (3), but requiring it to swim a certain distance or past physical features as a sperm selection method,
  iii. Flowing sperm through the well (3), perhaps repeatedly moving it back and forth over the oocyte to increase the chance of successful fertilization.
e. Washing away of sperm and cumulus cells from a recently fertilized embryo
f. Incubation/embryo culture
g. Media replacement/wash at prescribed times, or continuously during incubation
h. Cryo-preparation (replace water in the oocyte/embryo with cryoprotectant before vitrification)
i. Rewarming (replace cryoprotectant with water/media after vitrification)
j. Sampling and storage of culture media, separately and traceably for each well/embryo for non-invasive analysis (preimplantation genetic testing, proteomics, metabolomics) purposes.
k. Denudation (removal of cumulus cells) of an unfertilized oocyte
  i. via mechanical means, e.g. push/pull past or through features in the well (3) or adjoining channels (4),
  ii. with hyaluronidase as per existing manual protocols,
  iii. with lower concentration of hyaluronidase and over a longer time period than existing manual protocols.
l. Sperm selection and preparation, by one or more of:
  i. a swim or step challenge
  ii. a filter
  iii. capacitation.
m. Intracytoplasmic sperm injection (ICSI; potentially with additional, external equipment such as magnetic capture beads).
  i. Immobilize selected highly motile sperm by heat or chemical treatment that
  blocks mitochondria (sperm mitochondria are not needed after fertilization), or by letting
  the sperm swim to individual wells and then squash the tails with pressure.
  ii. Use microfluidic channel to hold oocyte in place for ICSI
  iii. Inject from above with piezo or other method.
n. Volume and/or fluid control.
  i. Each well (3) has two metal electrodes adjacent to the well, which act as capacitive sensors (19) to measure the height of the media/oil interface (or media/air interface). These sensors are used as a feedback loop to control the (positive and/or negative) pressure applied to the fluidic channels (4).
  ii. The biochip (100) can mix two reagent medias (for example culture and cryopreservation) at any ratio. Mixing is performed, by way of example, by one of:
  1) Joining both fluids into one channel 4 so the fluids flow adjacent to each other and mix by diffusion.

2) Use of microfluidic features that mix.
o. The biochip can carry out a range of cryo-preparation protocols, for example:
  i. Existing step-wise protocols (0%, 50%, 100% cryo-protectant concentrations)
  ii. Improvements with increasing numbers of steps
  iii. A continuous cryo-exchange, increasing the concentration of cryogenic fluid from 0% to 100% over a desired time period (e.g., between 7 and 20 minutes)
p. Fluid replacement, which can involve:
  i. Flowing fresh media in and pulling old media out, continuously, such that the fluid level in the well (3) remains constant.
  ii. Reducing the level of fluid in the well by pulling out old media, then replacing this fluid with fresh media, repeating as necessary.
  iii. Injecting a precise volume/dose of media/reagent.
q. Media sampling.
  i. The biochip (100) is arranged so that a small volume of fluid can be extracted from each well (3) and stored in storage pots (6) for later retrieval.

Example 3: Sampling of Embryo Culture Media

Figure 7:
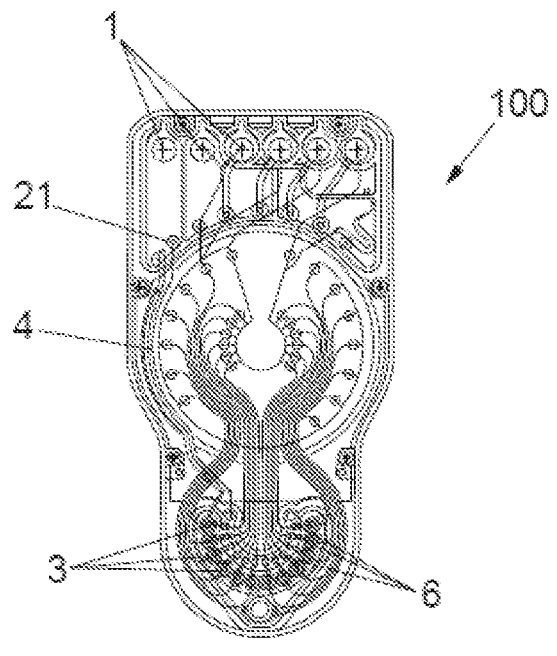
FIG. 7 shows a bottom view of a biochip with a single negative pressure channel connecting all sample reservoirs or storage pots.

Wells (3) are sampled by way of a pressure source (17) as shown in FIG. 7. A negative pressure port (21) and a negative pressure/vacuum channel (4), links to a common headspace and individual headspaces above all sampling pots (6) which are further linked to the wells (3) as shown in FIG. 8. Sampled media is stored in individual pots (6) (one corresponding to each well [3]) and these are covered by an air-permeable hydrophobic layer, mesh or paper (9) so that the common suction channel (4), or negative pressure channel (4), to all twelve functional wells (3), will fill all twelve reservoirs or pots (6). As soon as each individual pot (6) is full, the pressure required to draw liquid through air-permeable layer (9) is much higher than the pressure required to draw in more liquid to empty pots (6), so the first pot (6) does not overflow and consequently, the next pots in the sequence automatically continue filling. Embryo culture media can be analyzed off chip.

The pot (6) and filter paper (9) are covered with a layer of foil (8), which has two purposes: to create a sealed channel so that a negative pressure can be built up; and protect the pots (6) and the media therein until the user chooses to break the foil seal (8) and retrieves the sample media.

A second biochip performs well sampling in an alternative matter. An individual pot (6) connected to an individual well (3) via a microfluidic channel (4) and applying a negative pressure to the headspace of the pot (6) leads to pulling the liquid out from the well (3) to the pot (6).

Figure 9:
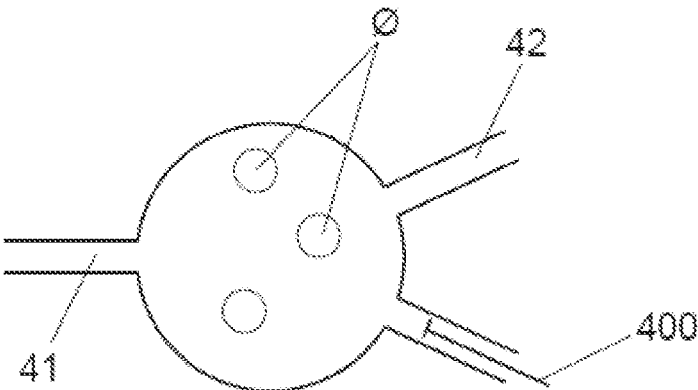
FIG. 9 shows a schematic view of a well with a channel for introducing a displacement pipette.

A third biochip performs well sampling via the use of a positive displacement plunger (400) as shown in FIG. 9. The well is connected to two or more channels (at least one inlet and at least one outlet) and further comprises at least one channel for the plunger (400) that can regulate, extract or even introduce in an automated way, volume of a fluid inside the well.

Example 4: Cradle Design

Figure 5:
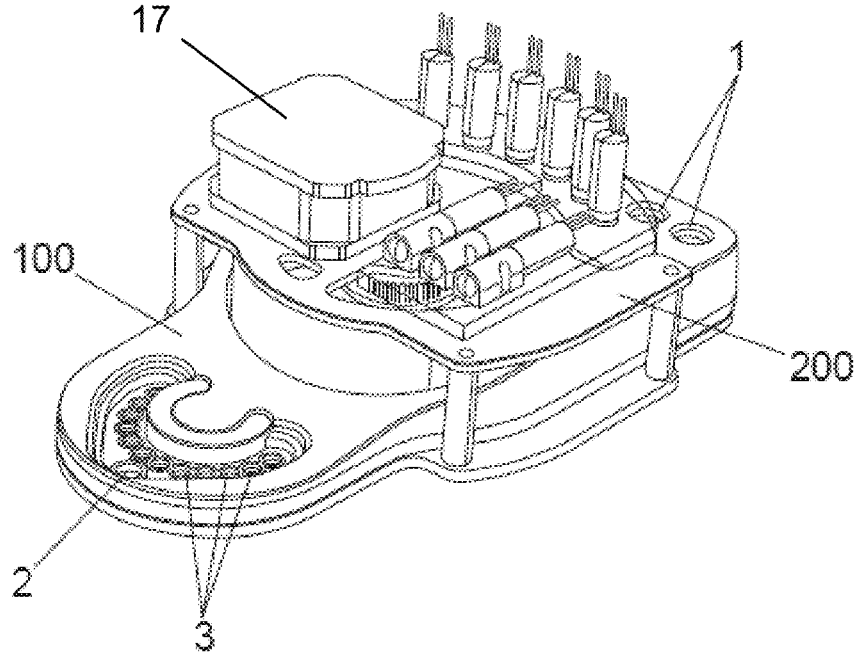
FIG. 5 shows a view of a cradle of the disclosure and a biochip positioned therein.
Figure 10:
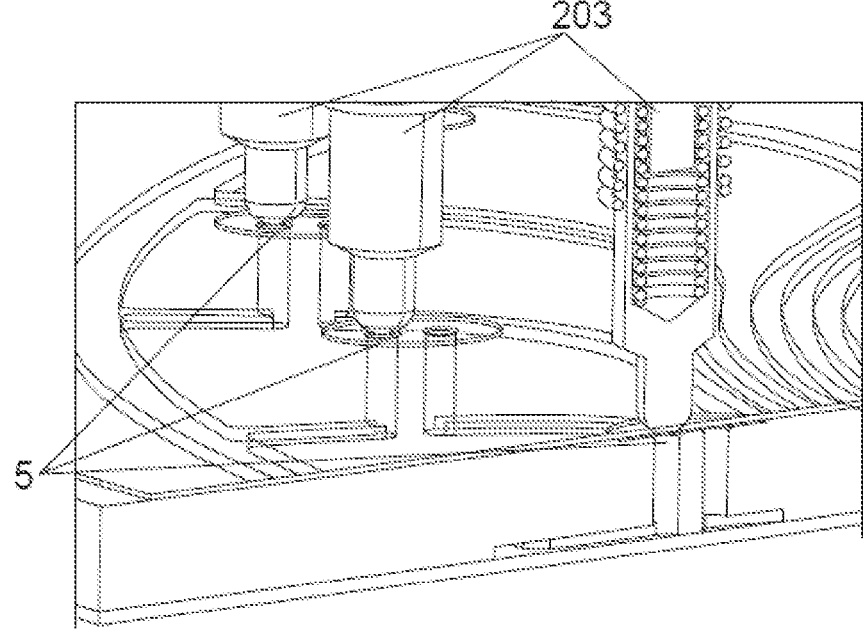
FIG. 10 shows activation pins that form part of the cradle of FIG. 5 engaging with valves on a biochip.

A cradle is constructed as shown in FIG. 5 and FIG. 10. The cradle (200) is a re-useable electro-mechanical assembly which interfaces mechanically and pneumatically with the biochip (100). As shown in FIG. 10, valve actuation pins (203), belonging to the cradle (200), interface with a fluidic valve (5) on the biochip (100). The cradle maintains required temperature conditions, and controls fluid motion in the biochip (100).

Three pumps are employed, two for pressuring the air in the reservoirs above the media (so that two of the media may be pushed simultaneously to the wells to achieve the full range of concentrations) and one for applying negative pressure to the air space on top of the pots or the waste reservoir (to pull liquids towards said pots or waste).

A series of membrane type fluidic valves control which paths the fluids take within the biochip. The actuator and other complex components are kept on the cradle (200) and interact with simple features on the biochip (100) to form a valve (5) as exemplified above.

To control fluidic valves with a single cam, a structure with four defined angular positions per well (3) is provided. The four positions are:

a. Inner valve (51) open, outer valve (52) closed
    b. Outer valve (52) open, inner valve (51) closed
    c. Both inner and outer valves (51), (52) open
    d. Both inner and outer valves (51), (52) closed.

Valves are configured to allow opening of channels to only one well (3) at a time to control the fluid flow to each well 3 accurately. (similar valve layouts that open more than one valve at a time are also possible in other configurations of biochip).

Example 5: Controlling Well Filling and Environment with a Cradle

Channels between reservoirs (1) and wells (3) are empty. One by one, fluids from reservoirs (1) are queued ready to flow to wells (3). The valves (51), (52) work as traffic lights in the sense that the valves control which fluid can go where, i.e., to which well (3) can each fluid from each reservoir (1) go. In the cradle/biochip configuration of this example, only one inner (51) and one outer (52) valve can be opened at the same time.

Additional valves are provided to link the pumps in the cradle (200) to the air space in the reagent reservoirs (1). These are on the cradle (200) and are shown as solenoid valves. These could be latching to reduce power consumption. They are arranged in a network to enable all the combinations of routing between pumps and reservoirs (1) but reducing the number of valves required.

Thermal control is achieved by positioning resistive heaters close to the wells (3). These heaters are discrete components on a printed circuit board (PCB), or alternatively, existing tracks used for other functions on the PCB are be employed. A temperature sensor measures the temperature close to the wells. A control system is provided on a microcontroller to drive the heaters by Pulse Width Modulation (PWM) relative to a set point that is programmable. The control system is a Proportional Integrated Derivative (PID). The ground plane of the PCB, which can be copper, carries the heat from heaters to the wells. The ground plane is then cut to prevent the heat being carried out of the biochip and heating the surroundings or the rest of the cradle. Routed Cuts can be made in the material of the PCB to prevent thermal conductivity. When the PCB is of FR4 type (which is insulating) routed cuts are not made. The heaters heat all the wells (3) evenly. The working well (2) at the front has a different geometry and uses additional heaters to maintain its temperature. Control of the heaters is independent of the top part of the cradle (200) so the base maintains a temperature whenever powered. Digital temperature sensors with an alarm feature control output and prevent overheating in the case of a temperature control loop error.

The cradle senses the liquid level in each of the wells (3) of the biochip (100). This sensing maintains closed loop control of the fluid level in each well. The sensor detects the exact level of the water oil interface in the well (3) and identifies when the fluid drops below a critical level or goes above a critical level. Sensing of the liquid level prevents emptying or overfilling. The level of the fluid in each well (3) is sensed with capacitive sensors, which have a capacitance between two electrodes that is sensitive to the fluid level in each well (3).

Features of the cradle that help the cradle carry out functions include:

The geometry of the cradle (200) complexed with a biochip (100) is compatible with imaging by a standard inverted microscope.

The distance from the surface to the bottom of the biochip (100) wells (3) (the imaging planes) is kept to a minimum to match the working distance of common objectives.

The area above the wells (3) is kept clear and the cradle (200) top part cut away to allow any condenser optics to get close enough to the wells (3).

The total area is similar to the size of a microscope stage.

The geometry of the cradle (200) complexed with a biochip (100) when combined is compatible with imaging by a standard stereo-microscope.

The total area of the cradle complexed with a biochip is similar to the area of a microscope stage.

The imaging planes are kept as close to the base as possible so that the image is in a very similar plane to the image from a petri dish on the same work surface. This configuration reduces the need for refocusing when moving between a petri dish and the biochip (100).

Example 6: Performing IVF with an Automated System of the Disclosure

Follicular fluid containing the cumulus oocyte complex (COC) is retrieved from a female subject that has previously undergone follicle stimulation. Six COCs are isolated from the follicular fluid and washed. Following COC isolation and washing, each COC is placed in a well of a biochip, which is complexed with a cradle. Reservoirs of the biochip are filled with oil, incubation medium, vitrification solution, fertilization medium, and sperm from a male donor though input ports on the biochip.

The cradle uses pneumatic force and the actuation of membrane valves to drive fertilization medium into the wells containing the COCs. Additionally, the cradle drives oil to cover the well and maintain stable conditions for the cells. After about 2 to about 6 hours the cradle uses pneumatic pressure to drive fluid containing the sperm through microchannels, towards the wells with the COCs. Pneumatic forces cease upon sperm reaching a capacitation area near the wells. The capacitation area contains physical features which sperm must swim through to reach the COCs in the well and serves as a method to select for motile sperm. Upon reaching the COC, the sperm is incubated with the COC for 16 hours. Following the 16 hour incubation, cradle drives embryo culture media into the well with the fertilized oocytes (now zygotes) and removes the sperm and fertilization media which contains detached cumulus cells. In some cases, the cradle performs additional washes with culture media containing small concentrations of hyaluronidase (10-100 IU). Oil is added to the well to maintain stable conditions for the embryo.

Throughout the fertilization and culture process, environmental control is provided by an incubator, which houses the cradle-biochip complex. Additionally, embryo development is monitored by an automated microscope system. On day 3 of embryo culture, the cradle provides pneumatic force and valve actuation to replace the embryo culture media.

After 5 days of embryo culture, the cradle drives a gradient of increasing concentrations of vitrification solution via pneumatic pressure and the actuation of valves. As wells fill with vitrification solution, embryo culture media is removed from wells into waste reservoirs or storage pots. Vitrification solution is added to wells such that the concentration of vitrification solution in the wells increases from 0% to 100% over a 15 minute period. After wells are filled with 100% vitrification solution, embryos are transferred to a separate component and stored in liquid nitrogen until the uterine transfer process occurs.

Embodiments

The following non-limiting embodiments provide illustrative examples of the devices, systems, and methods disclosed herein, but do not limit the scope of the disclosure.

Embodiment 1. A method comprising: (a) depositing a group of cells into a well, the well comprising: (i) an open upper end; (ii) a closed lower end; (iii) a perimeter body connecting the closed lower end and the open upper end; (iv) an inlet, wherein a size of the inlet in a first dimension is larger than a diameter of the group of cells and a size of the inlet in a second dimension is smaller than the diameter of the group of cells; (v) an outlet wherein a size of the outlet in a first dimension is larger than the diameter of the group of cells and a size of the outlet in a second dimension is smaller than the diameter of the group of cells; and (b) performing a liquid exchange, wherein the liquid exchange comprises: (I) flowing a first liquid into the well through the inlet; and (II) flowing a second liquid out of the well through the outlet; wherein performing the liquid exchange promotes embryo development of the group of cells.

Embodiment 2. The method of embodiment 1, wherein the group of cells is a group of embryonic cells.

Embodiment 3. The method of embodiment 1 or 2, wherein the group of cells is a single cell.

Embodiment 4. The method of embodiment 3, wherein the single cell is an oocyte.

Embodiment 5. The method of embodiment 1 or 2, wherein the group of cells is a mass of a plurality of cells.

Embodiment 6. The method of embodiment 5, wherein the mass of the plurality cells is a cumulus oocyte complex.

Embodiment 7. The method of embodiment 5, wherein the mass of the plurality of cells is a zygote.

Embodiment 8. The method of embodiment 5, wherein the mass of the plurality of cells is an embryo.

Embodiment 9. The method of embodiment 5, wherein the mass of the plurality of cells is a blastocyst.

Embodiment 10. The method of any one of embodiments 1-9, further comprising depositing the group of cells into the well through the open upper end.

Embodiment 11. The method of any one of embodiments 1-10, further comprising, prior to step (a), depositing the second liquid into the well through the open upper end.

Embodiment 12. The method of any one of embodiments 1-10, further comprising, prior to step (a), flowing the second liquid into the well through the inlet from a reservoir fluidically connected to the inlet by a channel.

Embodiment 13. The method of any one of embodiments 1-12, wherein the first liquid comprises a sperm cell.

Embodiment 14. The method of any one of embodiments 1-12, wherein the first liquid comprises an oil.

Embodiment 15. The method of any one of embodiments 1-12, wherein the first liquid is a fertilization medium.

Embodiment 16. The method of any one of embodiments 1-12, wherein the first liquid comprises a cryoprotectant.

Embodiment 17. The method of any one of embodiments, 1-12, wherein the first liquid is an embryo culture media.

Embodiment 18. The method of embodiment 17, wherein the embryo culture media comprises hyaluronidase.

Embodiment 19. The method of any one of embodiments 1-18, wherein the second liquid comprises a sperm cell.

Embodiment 20. The method of any one of embodiments 1-18, wherein the second liquid comprises an oil.

Embodiment 21. The method of any one of embodiments 1-18, wherein the second liquid is a fertilization medium.

Embodiment 22. The method of any one of embodiments 1-18, wherein the second liquid comprises a cryoprotectant.

Embodiment 23. The method of any one of embodiments 1-18, wherein the second liquid is an embryo culture media.

Embodiment 24. The method of embodiment 23, wherein the embryo culture media comprises hyaluronidase.

Embodiment 25. The method of any one of embodiments 1-24, further comprising, after (b), performing a second liquid exchange, wherein the second liquid exchange comprises: (III) flowing a third liquid into the well through the inlet; and (IV) flowing the first liquid out of the well through the outlet.

Embodiment 26. The method of any one of embodiments 1-25, wherein the well is fluidically connected to a reservoir by a channel, the method further comprising controlling a flow of liquid from the reservoir through the channel to the well via actuation of a valve.

Embodiment 27. The method of any one of embodiments 1-26, wherein the well is fluidically connected to a reservoir by a channel, the method further comprising controlling a flow of liquid from the reservoir through the channel to the well by a force.

Embodiment 28. The method of embodiment 27, wherein the force is a pneumatic force.

Embodiment 29. The method of embodiment 27, wherein the force is a hydraulic force.

Embodiment 30. The method of embodiment 27, wherein the force is a gravity force.

Embodiment 31. The method of any one of embodiments 1-30, further comprising flowing the second liquid from the outlet to a storage pot.

Embodiment 32. The method of any one of embodiments 1-31, further comprising: (c) connecting a negative pressure port to a storage pot, wherein the storage pot is covered by an air permeable medium and the storage pot is fluidically connected to the well; (d) drawing gas pressure through the negative pressure port out of the storage pot causing the second liquid to flow through the outlet into the storage pot such that the storage pot fills with the second liquid and the second liquid approaches the air permeable medium; and (e) ceasing to draw the second liquid into the storage pot when the second liquid contacts the air permeable medium.

Embodiment 33. The method of any one of embodiments 1-32, further comprising flowing the second liquid from the outlet to a waste container.

Embodiment 34. The method of any one of embodiments 1-33, The method of claim 1, further comprising immobilizing the group of cells within the well via suction.

Embodiment 35. The method of any one of embodiments 1-34, further comprising controlling a liquid temperature within the well.

Embodiment 36. The method of any one of embodiments 1-35, further comprising monitoring the group of cells within the well.

Embodiment 37. The method of embodiment 36, wherein monitoring the group of cells comprises viewing the group of cells under a microscope.

Embodiment 38. A method of collecting a conditioned media, the method comprising: (a) generating the conditioned media by culturing a group of cells in a media within a well, the well comprising: (i) an open upper end; (ii) a closed lower end; (iii) a perimeter body connecting the closed lower end and the open upper end; (iv) an outlet, wherein a size of the outlet in a first dimension is larger than a diameter of the group of cells and a size of the outlet in a second dimension is smaller than the diameter of the group of cells; (b) connecting a negative pressure port to a storage pot, wherein the storage pot is covered by an air permeable medium and the storage pot is fluidically connected to the well; (c) drawing gas pressure through the negative pressure port out of the storage pot causing the conditioned media to flow through the outlet into the storage pot such that the storage pot fills with the conditioned media and the conditioned media approaches the air permeable medium; and (d) ceasing to draw the conditioned media into the storage pot when the conditioned media contacts the air permeable medium.

Embodiment 39. The method of embodiment 38, wherein the group of cells is a group of embryonic cells.

Embodiment 40. The method of embodiment 38 or 39, wherein the group of cells is a single cell.

Embodiment 41. The method of embodiment 40, wherein the single cell is an oocyte.

Embodiment 42. The method of embodiment 38 or 39, wherein the group of cells is a mass of a plurality of cells.

Embodiment 43. The method of embodiment 42, wherein the mass of the plurality of cells is a cumulus oocyte complex.

Embodiment 44. The method of embodiment 42, wherein the mass of the plurality of cells is a zygote.

Embodiment 45. The method of embodiment 42, wherein the mass of the plurality of cells is an embryo.

Embodiment 46. The method of embodiment 42, wherein the mass of the plurality of cells is a blastocyst.

Embodiment 47. The method of any one of embodiments 38-46, further comprising, prior to (a), depositing the group of cells into the well through the open upper end.

Embodiment 48. The method of any one of embodiments 38-47, further comprising, prior to step (a), depositing a culture media into the well through the open upper end.

Embodiment 49. The method of any one of embodiments 38-48, wherein the well further comprises an inlet, wherein a size of the inlet in a first dimension is larger than the diameter of the group of cells and a size of the inlet in a second dimension is smaller than the diameter of the group of cells.

Embodiment 50. The method of embodiment 49, further comprising flowing a liquid through the inlet from a reservoir fluidically connected to the inlet by a channel.

Embodiment 51. The method of embodiment 50, wherein the liquid is an embryo culture media.

Embodiment 52. The method of embodiment 51, wherein the embryo culture media comprises hyaluronidase.

Embodiment 53. The method of embodiment 50, wherein the liquid comprises an oil.

Embodiment 54. The method of embodiment 50, wherein the liquid comprises a cryoprotectant.

Embodiment 55. The method of any one of embodiments 38-54 wherein the storage pot is fluidically connected to the well by a channel, the method further comprising controlling a flow of conditioned media from the well to the storage pot via actuation of a valve.

Embodiment 56. The method of any one of embodiments 38-55, further comprising immobilizing the group of cells within the well via suction.

Embodiment 57. The method of any one of embodiments 38-56, further comprising controlling a liquid temperature within the well.

Embodiment 58. The method of any one of embodiments 38-57, further comprising monitoring the group of cells within the well.

Embodiment 59. The method of any one of embodiments 38-58, wherein the air permeable medium is filter paper.

Embodiment 60. The method of any one of embodiments 38-58, wherein the air permeable medium is a hydrophobic filter.

Embodiment 61. The method of any one of embodiments 38-58, wherein the air permeable medium is a hydrophobic membrane.

Embodiment 62. A biochip comprising: (a) a first layer comprising a plurality of reservoirs; (b) a second layer comprising: (i) a plurality of channels imprinted in the second layer, wherein the channels are in fluidic communication with the reservoirs; (ii) a plurality of valves configured to control liquid flow within the plurality of channels; and (iii) a well imprinted in the second layer fluidically connected to the plurality of reservoirs by the plurality of channels, wherein the well comprises: (I) an open upper end; (II) a closed lower end; (III) a perimeter body connecting the closed lower end and the open upper end; (IV) an inlet; and (V) an outlet wherein the well contains a group of cells, the size of the inlet in a first dimension is larger than a diameter of the group of cells, the size of the inlet in a second dimension is smaller than the diameter of the group of cells, the size of the outlet in a first dimension is larger than the diameter of the group of cells, and the size of the outlet in a second dimension is smaller than the diameter of the group of cells; and (c) a housing encasing the first layer and the second layer.

Embodiment 63. The biochip of embodiment 62, wherein the first layer is directly on top of the second layer.

Embodiment 64. The biochip of embodiment 62 or 63, wherein the second layer further comprises: (iv) an upper film that seals the channels from the top; and (v) a lower film that seals the channels from the bottom.

Embodiment 65. The biochip of any one of embodiments 62-64, further comprising a plurality of input ports, wherein each of the plurality of input ports leads to at least one of the plurality of reservoirs.

Embodiment 66. The biochip of any one of embodiments 62-65, further comprising: (d) a plurality of orifices, wherein the plurality of orifices (16) is above the plurality of reservoirs; (e) a pressure source (17); and (f) a sealing layer in between and in contact with the plurality of reservoirs and the pressure source; wherein the sealing layer provides a pneumatic seal between the pressure source and the plurality of reservoirs.

Embodiment 67. The biochip of any one of embodiments 62-66, further comprising: (d) a storage pot imprinted in the second layer; and (e) an air permeable medium covering the storage pot.

Embodiment 68. The biochip of embodiment 67, wherein the air permeable medium is filter paper.

Embodiment 69. The biochip of embodiment 67, wherein the air permeable medium is a hydrophobic filter.

Embodiment 70. The biochip of embodiment 67, further comprising foil covering the air permeable medium.

Embodiment 71. The biochip of any one of embodiments 62-70, wherein the plurality of reservoirs is contained within a tray.

Embodiment 72. The biochip of any one of embodiments 62-71, wherein the second layer further comprises a negative pressure port.

Embodiment 73. The biochip of any one of embodiments 62-71, wherein the second layer further comprises a negative pressure channel.

Embodiment 74. The biochip of any one of embodiments 62-73, wherein the group of cells is a group of embryonic cells.

Embodiment 75. The biochip of any one of embodiments 62-74, wherein the group of cells is a single cell.

Embodiment 76. The biochip of embodiment 75, wherein the single cell is an oocyte.

Embodiment 77. The biochip of any one of embodiments 62-74, wherein the group of cells is a mass of a plurality of cells.

Embodiment 78. The biochip of embodiment 77, wherein the mass of the plurality of cells is a cumulus oocyte complex.

Embodiment 79. The biochip of embodiment 77, wherein the mass of the plurality of cells is a zygote.

Embodiment 80. The biochip of embodiment 77, wherein the mass of the plurality of cells is an embryo.

Embodiment 81. The biochip of embodiment 77, wherein the mass of the plurality of cells is a blastocyst.

Embodiment 82. The biochip of any one of embodiments 62-81, wherein the well further comprises a suction port.

Embodiment 83. The biochip of any one of embodiments 62-82, wherein the plurality of channels is a plurality of microfluidic channels.

Embodiment 84. The biochip of any one of embodiments 62-83, wherein the size of the inlet in the first dimension is about 120 µm to about 500 µm.

Embodiment 85. The biochip of any one of embodiments, 62-84, wherein the size of the inlet in the second dimension is of about 1 µm to about 60 µm.

Embodiment 86. The biochip of any one of embodiments 62-85, wherein the size of the outlet in the first dimension is about 120 µm to about 500 µm.

Embodiment 87. The biochip of any one of embodiments 62-86, wherein the size of the outlet in the second dimension is about 1 µm to about 60 µm.

Embodiment 88. The biochip of any one of embodiments 62-87, wherein a channel of the plurality of channels has a diameter of about 1 µm to about 10,000 µm.

Embodiment 89. The biochip of any one of embodiments 62-88, wherein the plurality of valves comprises a rotating valve.

Embodiment 90. The biochip of any one of embodiments 62-89, wherein the plurality of valves comprises a shuttle valve.

Embodiment 91. The biochip of any one of embodiments 62-90, wherein the plurality of valves comprises a gate valve.

Embodiment 92. The biochip of any one of embodiments 62-91, wherein the plurality of valves comprises a membrane valve.

Embodiment 93. The biochip of any one of embodiments 62-92, wherein the plurality of valves is configured to be controlled by a cradle.

Embodiment 94. The biochip of any one of embodiments 62-93, wherein the housing comprises an identifier corresponding to a subject, wherein the group of cells is derived from the subject.

Embodiment 95. A kit comprising: (a) a biochip of any one of embodiments 62-94; (b) an oil; (c) a cryoprotectant; (d) fertilization medium; and (e) embryo culture media.

Embodiment 96. A system comprising: (a) a biochip of any one of embodiments 62-94; and (b) an actuation cradle, wherein the biochip is fits into the actuation cradle.

Embodiment 97. The system of embodiment 96, wherein the plurality of valves is configured to be controlled by the actuation cradle.

Embodiment 98. The system of embodiment 96 or 97, wherein the actuation cradle comprises a plurality of activation pins.

Embodiment 99. The system of embodiment 98, wherein the plurality of activation pins is configured to engage with the plurality of valves.

Embodiment 100. The system of any one of embodiments 96-99, wherein actuation the cradle further comprises a sensor.

Embodiment 101. The system of embodiment 100, wherein the sensor is a temperature sensor.

Embodiment 102. The system of embodiment 100, wherein the sensor is a capacitive sensor.

Embodiment 103. The system of embodiment 100, wherein the sensor is a flow sensor.

Embodiment 104. The system of any one of embodiments 96-103, wherein the biochip comprises an identifier corresponding to a subject, the group of cells is derived from the subject, and the cradle is configured to identify the identifier.

Embodiment 105. The system of any one of embodiments 96-104, wherein the cradle comprises a power supply.

Embodiment 106. The system of any one of embodiments 96-105, wherein the cradle comprises a pump.

Embodiment 107. The system of any one of embodiments 96-106, further comprising an incubator, wherein the cradle is inserted into the incubator.

Embodiment 108. A biochip comprising at least one well for receiving and retaining an oocyte for manipulation; a plurality of reservoirs for retaining, in use, fluids for use in processing of the oocyte or associated zygote or embryo; a plurality of channels selectively connectable between the reservoirs and the well; and a plurality of valves, each associated with at least one respective channel and arranged such that, in use, they control connection between the reservoirs and the well such that a plurality of steps within an in vitro fertilization and/or vitrification method can be performed on the oocyte or embryo in use.

Embodiment 109. The biochip according to embodiment 108, wherein the reservoirs, channels and valves are arranged such that only one reservoir may be connected to the well at any one time.

Embodiment 110. The biochip according to embodiment 108 or 109, wherein the well is configured so that an oocyte can be placed therein, but is retained by a size of inlets and outlets within the well, the inlets and outlets further being sized such that they ensure free flow of fluid into and out of the well when an oocyte is in position.

Embodiment 111 The biochip according to embodiment 110, wherein the well is structured such that any oocyte, zygote or embryo placed therein in use are unable to enter a closed channel.

Embodiment 112. The biochip according to any one of embodiments 108-111, wherein the well is structured such that the location of any oocyte, zygote or embryo placed in the well in use is in substantially the same vertical plane as the plane of biochip.

Embodiment 113. The biochip according to any one of embodiments 108-112, wherein the well is configured such that the oocyte can be held in place by suction.

Embodiment 114. The biochip according to any one of embodiments 108-113, wherein the well is open to allow a user to load sperm/oocyte/zygote/embryo or remove the oocyte/zygote/embryo in use.

Embodiment 115. The biochip according to any one of embodiments 108-114, wherein the valves are arranged to be operated by an actuation cradle into which the biochip is inserted in use.

Embodiment 116. The biochip according to any one of embodiments 108-115, wherein the channels are of a size such that fluid can be driven through them either pneumatically or hydraulically.

Embodiment 117. The biochip according to any one of embodiments 108-116, wherein the well is transparent so that any oocyte/zygote/embryo positioned therein can be viewed during processing.

Embodiment 118. The biochip according to embodiment 117, wherein the well is structured with an optical access and physical structure so that any oocyte, zygote or embryo placed therein can be imaged on a standard inverted microscope.

Embodiment 119. The biochip according to any one of embodiments 108-118, wherein the reservoirs are configured so that they can be refilled and may have a structure to prevent overfilling.

Embodiment 120. The biochip according to any one of embodiments 108-119, wherein the reservoirs are structured so as to prevent incorrect filling.

Embodiment 121. A cradle for the biochip according to any one of embodiments 108-120, the cradle comprising plural activation pins for engaging with valves on a biochip when said biochip has been inserted in the cradle in use, the cradle further comprising means for controlling the activation pins to selectively operate the valves to perform at least one operation associated with an in vitro fertilization process.

Embodiment 122. The cradle of embodiment 121, further comprising a heater.

Embodiment 123. The cradle of embodiment 121 or 122, further comprising sensors for measuring the temperature on the biochip.

Embodiment 124. The cradle of any one of embodiments 121-123, further comprising sensors for monitoring reservoir levels within the biochip.

Embodiment 125. The cradle of any one of embodiments 121-124, further comprising a microprocessor for controlling the actuation pins, that control being dependent upon instructions set as pre-programmed on the microprocessor or controlled either directly or wirelessly through a remote control mechanism.

Embodiment 126. The cradle of any one of embodiments 121-125, further comprising its own power supply.

Embodiment 127. The cradle of any one of embodiments 121-126, further comprising means for identifying the biochip to ensure safety and reliability of the process.

Embodiment 128. A system comprising the biochip of any one of embodiments 108-120, and the cradle of any one of embodiments 121-127.

Embodiment 129. The system according to embodiment 128, further comprising an incubator.

What is claimed is:

1. A biochip comprising:
(a) a first layer comprising a plurality of reservoirs;
(b) a second layer comprising:
    (i) a plurality of channels imprinted in the second layer, wherein the channels are in fluidic communication with the reservoirs;
    (ii) a plurality of valves configured to control liquid flow within the plurality of channels; and
    (iii) at least one well imprinted in the second layer fluidically connected to the plurality of reservoirs by the plurality of channels,
wherein the well comprises:
    (I) an open upper end;
    (II) a closed lower end;
    (III) a perimeter body connecting the closed lower end and the open upper end;
    (IV) an inlet; and
    (V) an outlet
wherein:
    the well is dimensioned to receive a cell or a group of cells;
    the size of the inlet in a first dimension is larger than a diameter of the cell or group of cells;
    the size of the inlet in a second dimension is smaller than the diameter of the cell or group of cells;
    the size of the outlet in a first dimension is larger than the diameter of the cell or group of cells; and
    the size of the outlet in a second dimension is smaller than the diameter of the cell or group of cells;
    the well is placed between one inner valve placed before the inlet and one outer valve placed after the outlet;
wherein the second dimension of the inlet and the second dimension of the outlet become larger before joining one of the plurality of channels; and
(c) a housing encasing the first layer and the second layer.

2. The biochip of claim 1, wherein the second layer further comprises:
(iv) an upper film that seals the channels from the top; and
(v) a lower film that seals the channels from the bottom.

3. The biochip of claim 1, further comprising:
(d) a plurality of orifices, wherein the plurality of orifices is above the plurality of reservoirs;
(e) a pressure source; and
(f) a sealing layer in between and in contact with the plurality of reservoirs and the pressure source;
wherein the sealing layer provides a pneumatic seal between the pressure source and the plurality of reservoirs.

4. The biochip of claim 1, further comprising:
(d) a storage pot imprinted in the second layer; and
(e) an air permeable medium covering the storage pot.

5. The biochip of claim 1, wherein the well further comprises a suction port.

6. The biochip of claim 1, wherein each well has two adjacent metal electrodes acting as capacitive sensors.

7. The biochip of claim 1, wherein the closed lower end of the well is level with at least one of the plurality of channels.

8. A method comprising:
(a) depositing a cell or group of cells into a well of a biochip according to claim 1, (b) performing a liquid exchange, wherein the liquid exchange comprises:

(I) flowing a first liquid into the well through an inner valve and through the inlet; and (II) flowing a second liquid out of the well through the outlet and through an outer valve;

wherein the liquid exchange is performed to promote fertilization or embryo development of the group of cells.

9. The method of claim 8, further comprising, after (b), performing a second liquid exchange, wherein the second liquid exchange comprises:

(III) flowing a third liquid into the well through the inner valve and through the inlet; and (IV) flowing the first liquid out of the well through the outlet and through the outer valve.

10. The method of claim 8 further comprising:

(a) generating a conditioned media by culturing a cell or group of cells in a media within a well, (b) connecting a negative pressure port to a storage pot, wherein:

the storage pot is covered by an air permeable medium; and the storage pot is fluidically connected to the outlet through the outer valve;

(c) drawing gas pressure through the negative pressure port out of the storage pot causing the conditioned media to flow through the outlet and through the outer valve into the storage pot such that the storage pot fills with the conditioned media and the conditioned media approaches the air permeable medium; and (d) ceasing to draw the conditioned media into the storage pot when the conditioned media contacts the air permeable medium.

11. A system comprising:

(a) a biochip of claim 1; and (b) an actuation cradle, wherein the biochip fits into the actuation cradle.

12. The system of claim 11, wherein the plurality of valves is configured to be controlled by the actuation cradle.

13. The system of claim 11, wherein the actuation cradle comprises a plurality of activation pins engaging with the plurality of valves.

14. The system of claim 11, wherein the actuation cradle further comprises one or more temperature, capacitive, or flow sensors.

15. The system of claim 11, wherein the cradle comprises one or more pumps.

* * * * *